US012661082B2

(12) United States Patent
Kreisler et al.

(10) Patent No.: US 12,661,082 B2
(45) Date of Patent: Jun. 23, 2026

(54) METHOD FOR OPERATING A COMPUTED TOMOGRAPHY FACILITY AND COMPUTED TOMOGRAPHY FACILITY

(71) Applicant: Siemens Healthineers AG, Forchheim (DE)

(72) Inventors: Björn Kreisler, Hausen (DE); Benjamin Schweikert, Gutenstetten (DE); Florian Wolz, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 265 days.

(21) Appl. No.: 18/596,900

(22) Filed: Mar. 6, 2024

(65) Prior Publication Data

US 2024/0315659 A1      Sep. 26, 2024

(30) Foreign Application Priority Data

Mar. 23, 2023    (EP) ..................................... 23163685

(51) Int. Cl.
| | |
|---|---|
| *A61B 6/00* | (2024.01) |
| *A61B 6/03* | (2006.01) |
| *G06K 9/00* | (2022.01) |
| *G06T 12/20* | (2026.01) |

(52) U.S. Cl.
CPC ................ *A61B 6/56* (2013.01); *A61B 6/032* (2013.01); *A61B 6/54* (2013.01); *G06T 12/20* (2026.01); *G06T 2211/408* (2013.01)

(58) Field of Classification Search
USPC ....... 382/100, 128–133, 156, 168, 173, 181, 382/254, 305; 702/182; 378/19
See application file for complete search history.

(56) References Cited

U.S. PATENT DOCUMENTS

| | | | |
|---|---|---|---|
| 6,327,330 B1 | 12/2001 | Peter | |
| 7,191,093 B2 * | 3/2007 | Hein ...................... | A61B 6/583 |
| | | | 702/182 |
| 2017/0042494 A1 | 2/2017 | Kim | |
| 2018/0328866 A1 * | 11/2018 | Kang .................... | G01V 5/226 |

(Continued)

FOREIGN PATENT DOCUMENTS

| | | |
|---|---|---|
| DE | 19837442 A1 | 3/2000 |
| EP | 3760126 A1 | 1/2021 |

*Primary Examiner* — Seyed H Azarian
(74) *Attorney, Agent, or Firm* — Lempia Summerfield Katz LLC

(57) ABSTRACT

A method for operating a computed tomography facility includes, during an imaging process, dividing detector data into: (1) a first data stream with first detector data sufficient for the reconstruction of an evaluable computed tomography image dataset after completion of the raw data acquisition with the at least one X-ray detector with a data transmission rate corresponding at most to the maximum transmission rate; and (2) a second data stream comprising the remaining detector data as second detector data. The method further includes: transferring the first data stream as a real-time transmission directly to a computing facility via a communication path; storing the second detector data in a temporary storage facility; and, after completion of the raw data acquisition with the at least one X-ray detector and the transmission of the first data stream, transmitting the second detector data to the computing facility via the communication path.

15 Claims, 3 Drawing Sheets

(56) References Cited

U.S. PATENT DOCUMENTS

| | | | |
|---|---|---|---|
| 2021/0000434 A1* | 1/2021 | Drapkin | A61B 6/4266 |
| 2022/0202383 A1* | 6/2022 | Okajima | A61B 6/4241 |
| 2023/0000458 A1* | 1/2023 | Bergner | A61B 6/032 |
| 2023/0277152 A1* | 9/2023 | Kim | A61B 6/4241 |
| | | | 378/19 |
| 2023/0293135 A1* | 9/2023 | Maltz | A61B 6/56 |

* cited by examiner

METHOD FOR OPERATING A COMPUTED TOMOGRAPHY FACILITY AND COMPUTED TOMOGRAPHY FACILITY

The present patent document claims the benefit of European Patent Application No. 23163685.3, filed Mar. 23, 2023, which is hereby incorporated by reference in its entirety.

TECHNICAL FIELD

The disclosure relates to a method for operating a computed tomography facility that has a rotatable portion with at least one X-ray detector and a portion that is fixed relative to the rotatable portion with a computing facility configured to process detector data recorded with the at least one X-ray detector, wherein the at least one X-ray detector is assigned a preparation facility for ascertaining detector data to be transmitted to the computing facility via a communication path from raw data of the at least one X-ray detector and the communication path has a wireless communication link with a maximum transmission rate. In addition, the disclosure relates to a computed tomography facility.

BACKGROUND

Computed tomography facilities are known in the art and may have at least one recording arrangement with an X-ray source and an X-ray detector that may be rotated about a patient or other object to be examined. Hence, the recording arrangement with the X-ray source and the X-ray detector belongs to a rotatable portion of the computed tomography facility that may be guided in a gantry of the computed tomography facility that belongs to the fixed portion. In order to be able to ascertain computed tomography image datasets, raw data recorded with the at least one X-ray detector that may be prepared on site by a preparation facility to form detector data that is transmitted to a computing facility of the computed tomography facility that belongs to the fixed portion and is frequently also referred to as an image computer. The image computer uses the detector data to reconstruct a computed tomography image dataset, for example, a set of sectional images and/or a three-dimensional image volume.

In order to provide the greatest possible freedom of movement of the rotatable portion, in particular to allow rotational runs over large angular intervals, (e.g., complete rotations), it has been proposed that a wireless communication link be provided on the communication path from the preparation facility to the computing facility. However, for technical reasons, the maximum transmission rate of the wireless communication link is limited so that, for example, a maximum of 25 to 30 Gbit/s may be transmitted. Current X-ray detectors, in particular so-called counting X-ray detectors (counting detectors), generate raw data internally with a much higher data rate, in particular if a plurality of X-ray detectors are provided. This may be the case if the computed tomography facility is a biplane computed tomography facility in which the rotatable portion has two recording arrangements at an angle to one another with respective X-ray detectors. For example, two counting X-ray detectors may result in raw data rates of several hundred Gbit/s.

In the case of computed tomography facilities or X-ray facilities in general, there is a requirement for applied X-rays to be translated into a diagnosable X-ray image in each case. This means that, even in the event of a system failure, (e.g., a power failure, an error along the communication path, and/or another interruption), recorded detector data is already persistently stored in the computing facility and it is possible to reconstruct a computed tomography dataset. This means that real-time transmission of the detector data is provided.

To make this possible, in known computed tomography facilities, the preparation facility processes the raw data in such a way that a data stream of detector data is created with a transmission rate (data rate) of less than or equal to the maximum transmission rate. For this purpose, it is, for example, known to reduce the spatial resolution of the preparation facility, in the case of counting X-ray detectors, to select and transmit detector data assigned to only a low number of energy threshold values and/or to use compression methods. The latter include, for example, hybrid data coding and differential statistical data coding. To reduce the spatial resolution, it is, for example, known to combine four pixels on the X-ray detector (2×2). This process may also be referred to as "fusing."

In this way, it is possible to meet the requirements for real-time transmission and to generate a data stream of detector data with a transmission rate during direct transmission (real-time transmission) that is lower than or equal to the maximum transmission rate of the wireless communication link. After each time step in which the at least one X-ray detector is read, measured information may be sent in very small packets and stored on the image computer, i.e., computing facility.

If short-term transmission errors occur, it has been proposed that a FIFO buffer memory be used in order to enable a resend. Although this may lead to minor delays, if the raw data acquisition is interrupted, apart from very few small data packets, the detector data measured so far is already available on the computing facility.

With known computed tomography facilities, this leads to severe restrictions when high-precision information is required. For example, it is known that in order to be able also to use the high spatial resolution of the at least one X-ray detector, the number of transmitted detector rows is restricted in return in order to maintain the maximum transmission rate. The use of further energy threshold values of the at least one X-ray detector may result in the spatial resolution having to be reduced more significantly.

SUMMARY AND DESCRIPTION

The scope of the present disclosure is defined solely by the appended claims and is not affected to any degree by the statements within this summary. The present embodiments may obviate one or more of the drawbacks or limitations in the related art.

The disclosure is based on the object of also allowing more data-intensive imaging processes in computed tomography facilities despite the use of a wireless communication link and the requirement for a computed tomography image that is present even in the event of an interruption or system failure.

To achieve this object, a method is disclosed such that, during an imaging process: a selection unit of the preparation facility divides the detector data into a first data stream with first detector data that is sufficient for the reconstruction of an evaluable computed tomography image dataset after completion of the raw data acquisition with the at least one X-ray detector with a data transmission rate corresponding at most to the maximum transmission rate and a second data stream including the remaining detector data as second detector data; the first data stream is transferred as a real-time transmission directly to the computing facility via the communication path; the second detector data of the second data stream is temporarily stored in a temporary storage facility; and, after completion of the raw data acquisition with the at least one X-ray detector and the transmission of the first data stream, the second detector data is transmitted to the computing facility via the communication path.

Here, the detector data of the second data stream may also be stored in the temporary store in real time, so that the raw data stream that forms in the at least one X-ray detector may be processed in real time by the preparation facility and the detector data formed may be divided into the data streams by the selection unit. Therefore, this results in a continuous real-time data flow. Herein, the data transmission rate required for unbuffered transmission (real-time transmission) of the first and the second data stream together would be greater than the maximum transmission rate. In particular, it is even conceivable that the data transmission rate for unbuffered transmission (real-time transmission) of the second data stream alone is greater than the maximum transmission rate.

In certain examples, the preparation facility may also be configured to compress detector data by a compression method, as is known in principle in the art. However, the preparation facility also initializes the detector data for transmission in other ways, in particular by selection and/or formatting and/or another type of preprocessing. The preparation facility may furthermore be configured to adapt the spatial and/or temporal resolution of detector data and/or to ascertain a frequency representation of the detector data, as discussed in greater detail below.

The disclosure is based on the idea of presorting the detector data in such a way that, to ascertain a computed tomography image dataset, sufficient, important first detector data is initially transmitted directly unbuffered to the computing facility, i.e., the image computer, and stored there, while second detector data is assigned a lesser importance with respect to the requirement for sufficient detector data to be available for the reconstruction of a computed tomography dataset and this is initially stored temporarily in order to be transmitted in the follow-up. This means that the transmission of the first detector data in the first data stream and the transmission of the second detector data are performed one after the other. In this way, it may be provided that a complete scan takes place at all times and also that sufficient portions for ascertaining a computed tomography dataset are immediately sent to the computing facility and stored there. The fact that the first detector data is sufficient for the reconstruction of an evaluable computed tomography image dataset after completion of the raw data acquisition with the at least one X-ray detector may be understood as meaning that it fulfills a prespecified minimum data criterion. Further information is only sent to the computing facility after the end of the raw data acquisition (and the transmission of the first detector data). This follow-up increases the data volume and thus also the information content of the available detector data. Hence, as a result of the selection made and the time delay, more detector data may be transmitted, wherein a complete computed tomography image dataset is still available for diagnosis directly at the end of the raw data acquisition (end of scan). Further information, such as higher spatial resolution or further spectral information, is available with a delay and may be used accordingly in the subsequent process.

In order to presort the detector data in this way, a different type of action directly in the preparation facility is proposed, so that a selection unit is proposed in order to generate two different data streams. The first data stream is provided for direct transfer to the image computer, i.e., the computing facility, while the second data stream is forwarded, for example, by a corresponding temporary storage unit, for temporary storage in a temporary storage facility in order to be transferred with a delay after the end of the raw data acquisition. Herein, as already explained, these two data streams are so to speak filled synchronously.

While previously the data rate was limited by the maximum transmission rate for direct transfer and higher data rates were consistently prevented, the solution presented here may enable data rates or data volumes that have not yet been achievable with current data transmission technology. All that is required for this is for a suitably large temporary storage facility to be provided in the rotatable portion, possibly as part of the preparation facility.

Herein, the X-ray detector may be a so-called counting X-ray detector, i.e., an X-ray detector configured to count individual photons. A counting X-ray detector may be configured not only to detect individual quanta, but additionally also to quantify the energy of the photon, so that spectral imaging, i.e., imaging with energy resolution, is enabled. For this purpose, different energy threshold values may be used in the X-ray detector. In certain examples, the computed tomography facility may be a biplane computed tomography facility in which the rotating portion therefore has two recording arrangements with an X-ray source and an X-ray detector in each case. These may be arranged rotated by 90° relative to one another. In this case, there are therefore two X-ray detectors the raw data of which may be prepared in a common preparation facility or also in separate preparation facilities for transfer to the computing facility.

Here, in the context of the present disclosure, different possibilities are conceivable as to how first detector data may be specifically selected for the first data stream, for example, also with regard to previous preparation by the preparation facility. In particular, in comparison to the entire detector data, spatial, temporal, and/or spectral reduction may take place. These options may also be used in combination with one another. In particular, with a combination of such reduction techniques, it is particularly advantageously possible to perform the division so that the maximum transmission rate is utilized as far as possible. This means it may be expedient to utilize the maximum transmission rate as far as possible when transmitting the first data stream in order to be able to minimize the follow-up accordingly. This may also be expedient in conceivable cases in which first detector data is created and provided specifically for the first data stream, for example by reducing the spatial resolution compared to the corresponding information still contained in the second detector data. This is because a computed tomography image dataset of the highest possible quality is then provided, even if the second detector data is no longer transmitted.

Specifically, it may be provided that the first data stream includes first detector data that is at least partially reduced in spatial resolution and/or spatial coverage compared to the entire detector data, in particular also the second detector data alone. In certain embodiments that use such spatial sorting, detector data is (e.g., initially) omitted and/or detector data is offset against one another in order to reduce the spatial resolution. In the second case, it may also be provided that the reduction in spatial resolution is specifically used to create the first detector data for the first data stream, i.e., initially, detector data with a lower spatial resolution is sent. A diagnostically usable computed tomography image dataset may already be ascertained from this. In a second act, second detector data with higher spatial resolution may then be supplied. The spatial resolution may be reduced by combining detector values of a group of adjacent pixels, for example 2×2 or 3×3 pixels into a new pixel. Accordingly, this results in a reduction in the data volume by a factor of four or nine. For example, counting X-ray detectors are already known with a pixel size in the range of 300 μm, so that a combination of nine pixels may remain below a pixel size of 1 mm.

A further possibility for reducing the data volume in spatial terms is to omit certain data, for example a certain number of detector rows and/or detector columns whose detector data is then supplied as second detector data. For example, in the prior art, it has already been proposed for some applications that only a certain number of detector rows be transmitted for each time step in order not to exceed the maximum transmission rate. The rest of the data had to be discarded. In the context of the present disclosure, this remaining detector data may be sorted into the second data stream and temporarily stored so that it may be supplied later.

In this context, embodiments are also conceivable in which regular omissions are made with respect to detector rows and/or detector columns, for example only every $n^{th}$ row and/or every $n^{th}$ column is transmitted. As will be discussed in more detail below, this opens up the option for the computing facility to estimate missing second detector data, i.e., data that is only transmitted at a later time or has been lost, by interpolation and/or extrapolation and to complete the detector dataset again, at least as an estimate.

Herein, it is not necessary for the same spatial omission to take place for each time step in which the at least one X-ray detector is read, and new raw data is formed and/or in which new detector data is prepared. For example, a pre-specified overall spatial coverage of the entire detector data may be split into at least two subgroups, wherein the raw data acquisition takes place in time steps and in each case only the detector data of one of the subgroups is selected into the first data stream in successive time steps according to a prespecified sequence of the subgroups. For example, detector rows with even row numbers and detector rows with odd row numbers may be transmitted alternately in time steps; it is also conceivable to alternate between the upper and lower half or the left and right half. Further subdivisions into subgroups may also be possible. One example of such sampling is a type of "even-odd reading structure" in which a different spatial structure is transmitted in every $n^{th}$ time step, i.e., reading, and then in each case omitted detector data is transmitted in the follow-up in order to obtain the full information. This may improve interpolations to be performed.

In principle, temporal sorting is also conceivable. Here, it may therefore be provided that the temporal resolution of the first detector data is lower than that of the entire detector data. For example, it may also be provided here that the raw data acquisition takes place in time steps, wherein the first data stream includes only detector data from every $n^{th}$ time step and the remaining detector data is assigned to the second data stream. In this case, only every $n^{th}$ reading is transmitted immediately and all detector data that has been omitted for the time being is transmitted in the follow-up, so that full temporal resolution is achieved. Herein, one embodiment provides that, during the transmission of the detector data of each $n^{th}$ time step in the first data stream, a sum and/or an average value over several time steps, here n time steps, is ascertained and transmitted.

Furthermore, frequency-based sorting may also be conceivable in order to take spatial and/or temporal variations into account. For example, it may be specifically provided that the preparation facility has a transformation unit for ascertaining a spatial frequency representation of the detector data, wherein only detector data with spatial frequencies that satisfy a spatial frequency criterion are sorted into the first data stream. Thus, it is, for example, proposed that methods such as those used in image composition when streaming videos are transferred for use on a computed tomography facility, wherein initially only certain spatial frequencies are transmitted, and the missing information is only transmitted downstream. Therefore, the selection may be performed based on the spatial frequencies that occur (wavelets or also spatial frequencies). For example, it is conceivable to use the spatial frequency criterion to check whether the spatial frequency is below a spatial frequency threshold. In this case, initially only the low spatial frequencies are transmitted, so that initially a coarser image is formed before refinement takes place with the follow-up of the second detector data. However, other selection options are also conceivable that are mapped by the spatial frequency criterion, so that, for example, successive spatial frequency intervals may be assigned alternately to the first detector data and the second detector data.

If detector data is omitted spatially and/or temporally and/or frequency-based for the first data stream, as already indicated, it may be provided that, on the reconstruction of a computed tomography image dataset from the detector data of the first data stream alone, at least a part of the omitted detector data is reconstructed by interpolation and/or extrapolation. This is in particular also expedient with regard to splitting with respect to spatial frequencies, since then a usable supplemented detector dataset is formed on the receiver side, i.e., the computing facility, by interpolation, in which estimated detector data may be replaced on the basis of follow-up data parts, i.e., second detector data, so that a complete detector dataset is obtained over time. Interpolation may take place by linear regression, wherein more complex regression methods, for example non-linear regression, may also be used. Finally, it is also conceivable to use methods based on artificial intelligence, for example, "super-resolution," or methods that are also used for dynamic construction when zooming in on maps on the internet and/or with variable data rates when streaming videos.

Herein, it may be expedient to reconstruct a provisional computed tomography image dataset from the first detector data, possibly already online during receipt, and to display it. In this way, a user is also made aware that, even in the event of an interruption or system failure, useful data is already available and the user may then accordingly visually track the improvement or expansion of this data on the arrival of the second detector data.

In a further possibility for selecting detector data, it may be provided that the computed tomography facility is configured for spectral imaging and the detector data includes partial data assigned to different energy parameter values, wherein the first data stream only contains partial data for some of the plurality of energy parameter values. For example, as already explained, the at least one X-ray detector may be a counting X-ray detector and acquire the detector data for a plurality of energy threshold values as energy parameter values, wherein the first data stream includes as first detector data only partial data of at least one of the energy threshold values, in particular the lowest energy threshold value. In this case, therefore, spectral sorting is provided, wherein different partial data is transmitted during the immediate transmission of the first data stream than in the follow-up. In this way, the energy resolution capability of the at least one X-ray detector may be used more extensively by the follow-up information, i.e., the second detector data.

Herein, combinations of these selection techniques may also be conceivable. For example, it is possible that the spatial resolution is reduced by the preparation facility for the partial data of the lowest energy threshold value, wherein the detector data formed is then sorted into the first data stream as first detector data. The higher resolution detector data of the lowest energy threshold value and the detector data of other energy threshold values (which may nevertheless still have reduced spatial resolution) are initially temporarily stored as second detector data and transmitted in the follow-up.

Herein, particularly advantageously, the selection may be parameterizable. For example, embodiments of the method may provide that the selection unit performs the division according to at least one selection parameter that may be prespecified by a control facility of the computed tomography facility. For example, different selection parameters may be assigned to different recording protocols, which, on the one hand, use the maximum transmission rate as far as possible in the first data stream for this recording protocol and, on the other hand, provide the coarse information required for the specific imaging task with the first data stream and further desired information as the second detector data in the follow-up. In this regard, in many cases the recording protocols may also already be assigned preparation parameters for the preparation facility in general, which define the ascertaining of the detector data and hence the type of detector data to be ascertained.

Herein, it may specifically be provided that the at least one selection parameter is transferred to the preparation facility by the control facility together with at least one preparation parameter that parameterizes the preparation. Herein, at least one of the at least one processing parameter may be directly related to the selection. For example, for maximum use of the maximum transmission rate, at least one of the at least one preparation parameter may be selected such that detector data for the first data stream is formed in a suitable volume per time unit, for example, by changing the spatial resolution and/or adapting a compression. In other words, the desired information for each recording protocol is already known in advance and may therefore be used to set the preparation facility accordingly, for example during the so-called "scan load," in which the components of the rotating portion of the computed tomography facility are also initialized accordingly by the control facility by parameterization.

In particular, this means that the at least one corresponding selection parameter is assigned to each selectable recording protocol specifying acquisition parameters for the raw data acquisition and/or preparation parameters for the preparation and is transferred to the preparation facility and set there before the start of the raw data acquisition. For example, the at least one selection parameter may be stored together with the at least one acquisition parameter and/or the at least one preparation parameter in a look-up table of the control facility.

It is particularly expedient if the at least one selection parameter and/or selection information describing the division into the data streams is also transferred to the computing facility, where, in an initialization act, the received detector data of the first data stream and the second data stream are combined to form a detector dataset suitable as input data for subsequent data processing operations of the computing facility. In this way, the computing facility, (e.g., the image computer), may be informed of the way in which the detector data is divided into the first and the second data stream and how it reaches it, so that for downstream reconstruction acts, to ascertain the final computed tomography image dataset, a dedicated initialization act may be provided that generates an overall detector dataset in a sorting expected by the downstream reconstruction acts. In this way, computed tomography image datasets may be ascertained in the same way, regardless of how the selection and transmission took place. In other words, subsequent computing acts no longer require knowledge of the "scrambled" data transmission of the detector data.

Expediently, for transmissions via the communication path, a buffer memory may be used that allows a data packet of the first and/or second detector data to be resent in the event of a faulty transmission. The provision of such buffer memories that allow resending is already known in principle in the prior art. As explained in the introduction, the first data stream is sent in real time, i.e., immediately, when new first detector data is available in each time step. Herein, these may not be very large data packets. However, this also means that if a transmission error occurs, there is only a brief time offset.

In an expedient development, the buffer memory may be implemented as part of the temporary storage facility reserved for this purpose. This enables only one single storage facility to be provided that provides the memory space as a temporary store for the second detector data and the buffer memory for data transmissions via the communication path. Therefore, the temporary storage facility includes a smaller portion of the storage space there, which serves as a real buffer for resending during direct transmission, and a larger portion of a storage space in which second detector data is stored and transmitted after the end of the raw data acquisition.

In one embodiment, during the transmission of the detector data of the second data stream, initialization information for the next imaging process is already transferred to the rotating portion. This expediently makes it possible to work in a time-efficient manner and to start the next imaging process directly after completion of the transmission of the second detector data to the computing facility. Handling of this type is expedient if data transmission via the wireless data transmission link may take place in parallel in both directions so that no portion of the maximum transmission rate is required for this initialization process or a portion of the maximum transmission rate "remains free."

In advantageous embodiments, it may be provided that, in the event of only partial transmission of the second detector data that includes additional information compared to the first detector data due to an error, in particular a system failure, the computing facility is configured to add the additional information in the computed tomography image dataset at least with respect to the transmitted part. This means that the handling of detector data on the computing facility, in particular also with respect to the initialization act already discussed, is selected in such a way that the transmitted part may still be used usefully even in the case of partial transmission of the second detector data. For example, then at least part of the computed tomography image dataset may be ascertained and depicted in high spatial resolution and/or additional spectral information may be displayed in at least part of the computed tomography image dataset. Corresponding techniques for detector data processing are in principle already known in the art.

In addition to the method, the disclosure also relates to a computed tomography facility with a rotatable portion with at least one X-ray detector and a portion fixed relative to the rotatable portion with a computing facility configured to process detector data recorded with the at least one X-ray detector, wherein the at least one X-ray detector is assigned a preparation facility for ascertaining detector data to be transmitted to the computing facility via a communication path from raw data of the at least one X-ray detector and the communication path has a wireless communication link with a maximum transmission rate.

According to the disclosure, the preparation facility includes a selection unit for dividing the detector data of an imaging process into a first data stream with first detector data that is sufficient for the reconstruction of an evaluable computed tomography image dataset after completion of the raw data acquisition with the at least one X-ray detector with a data transmission rate corresponding at most to the maximum transmission rate and a second data stream including the remaining detector data as second detector data. The preparation facility further includes a temporary storage unit for temporarily storing the second detector data of the second data stream in a temporary storage facility. The preparation facility further includes a transmission unit for direct real-time transmission of the first data stream via the communication path to the computing facility and, after completion of the raw data acquisition of the imaging process and the transmission of the first detector data, for transmission of the second detector data via the communication path to the computing facility.

All explanations of the method disclosed herein may be transferred analogously to the computed tomography facility so that the advantages already mentioned may also be obtained therewith. Here, the preparation facility may also have further functional units, in particular preparation units for ascertaining detector data from the raw data of the at least one X-ray detector. The temporary storage facility may be provided as part of the preparation facility, in particular in a common housing with the preparation facility. As explained, the at least one X-ray detector may be a counting X-ray detector and/or the computed tomography facility may be implemented as a biplane computed tomography facility.

BRIEF DESCRIPTION OF THE DRA WINGS

Further advantages and details of the present disclosure emerge from the embodiments described below and with reference to the drawings. The figures show:

DETAILED DESCRIPTION

Figure 1:
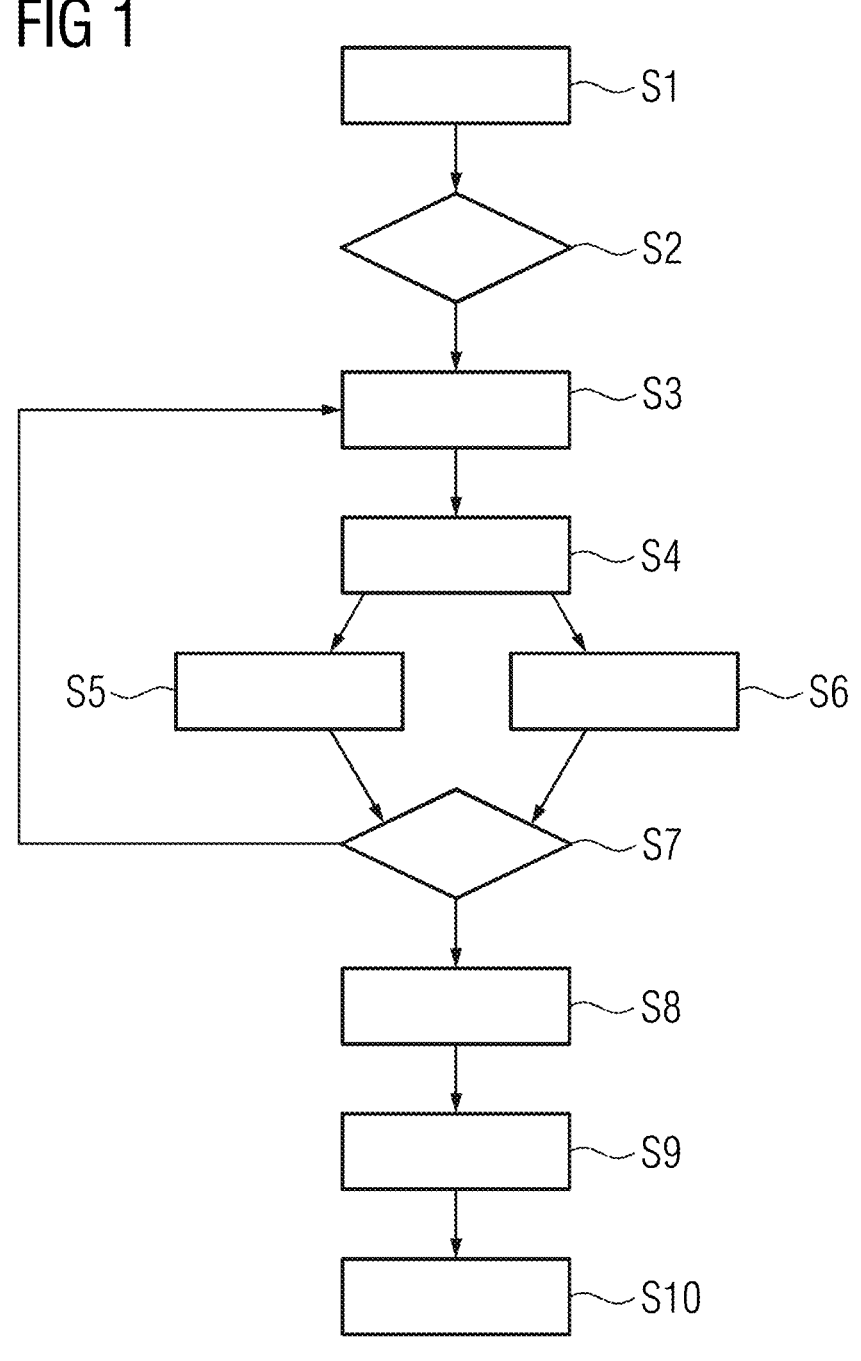
FIG. 1 depicts a flow chart of an embodiment of the method.

FIG. 1 shows a flow chart of a method for operating a computed tomography facility during the performance of an imaging process on an object, e.g., a patient. Herein, the patient is placed in a gantry of the computed tomography facility in such a way that at least one recording arrangement of the computed tomography facility including an X-ray source and an X-ray detector may be rotated around the patient, more precisely a recording area of the patient. Therefore, the recording arrangement belongs to a rotatable portion of the computed tomography facility, which may be rotated against a fixed portion, for example, the gantry. Further fixed items are a computing facility of the computed tomography facility serving as an image computer and a control facility controlling the operation of the computed tomography facility, wherein the computing facility may form part of the control facility. In order to be able to transfer information for actuation to the components of the rotatable portion of the computed tomography facility and to transmit detector data acquired by the at least one X-ray detector and provided by a preparation facility, which also forms part of the rotatable portion, to the computing facility, a communication path is provided, which, in the present case, includes a wireless communication link for establishing ideal rotational mobility. The wireless communication link has a maximum transmission rate, which means that a data stream with a data transmission rate that is greater than the maximum transmission rate cannot be transmitted unbuffered in real time via the wireless communication link and hence the communication path.

Nevertheless, it is a requirement for computed tomography facilities that, even in the event of system failure or another interruption to the scan, detector data that has already been acquired may be persistently stored and used in order to reconstruct a diagnosable computed tomography image. The method described below represents a possibility of fulfilling this requirement while still providing additional more detailed information.

In act S1, the control facility sends control information via the communication path to the actuatable components of the rotatable portion in order to initialize the raw data acquisition with the at least one detector. Herein, the control information includes, on the one hand, preparation parameters that indicate how the raw data of the at least one X-ray detector is to be prepared to form detector data to be transmitted to the computing facility. On the other hand, however, the control information also contains selection parameters for parameterizing a selection unit of the preparation facility in which the detector data formed in each time step is divided into a first data stream that is to be transmitted immediately to the computing facility and a second data stream with second detector data that is stored in a temporary storage facility, which here is integrated into the preparation facility, and is only transferred to the computing facility after completion of the first data stream and the raw data acquisition. Herein, the preparation parameters and the selection parameters are coordinated with one another, in particular also in such a way that the data transmission rate of the first data stream comes as close as possible to the maximum transmission rate of the wireless communication link. Selection information describing the division into the data streams is also transferred to the computing facility so that detector data received there in an initialization act may ultimately be continuously sorted (and possibly decompressed) so that it may be processed in subsequent reconstruction acts, i.e., delivered in a desired format. Thus, the reconstruction acts themselves do not require any knowledge of the special data transmission described here.

Here, the preparation parameters and the selection parameters and also the selection information may be assigned to a selected recording protocol for the imaging process, for example, by a look-up table in the control facility. Herein, the assigned control information may also include further acquisition parameters for the raw data acquisition.

Then, in act S2, the raw data acquisition begins, after which, for each time step in which the at least one X-ray detector measures raw data, this data is prepared in act S3 by the preparation facility in order to ascertain detector data. For this purpose, the preparation facility may have preparation units, which, for example, in addition to establishing a desired format and desired sorting, may also perform data compression and/or may at least partially reduce spatial resolution and the like.

In act S4, the selection unit of the preparation facility divides the incoming detector data stream into the first data stream and the second data stream, for which purpose, for example, selection criteria parameterized by the selection parameters may be used. Examples of such selection criteria and how to stay below the maximum transmission rate are discussed in more detail below.

Acts S5 and S6 then run in parallel. In act S5, the first data stream with the first detector data, in particular a data packet for each time step, is further transmitted directly via the communication path to the computing facility. However, buffering via a small buffer memory that allows individual data packets to be resent only takes place in the event of a transmission error. This provides real-time transmission. Act S5 may take place by a transmission unit of the preparation facility. In parallel, in act S6, a temporary storage unit forwards the second data stream with the second detector data into the temporary storage facility where it is stored temporarily. Herein, incidentally, the small buffer memory with respect to act S5 may be provided as a small portion of the temporary storage facility.

In act S7, a check is then performed as to whether further time steps are to follow or whether the raw data acquisition has been completed. If further time steps follow, act S3 is continued accordingly.

If the raw data acquisition is complete, in act S8, after the transmission of the first data stream has also been completed, the second detector data is transmitted from the temporary storage facility by the transmission unit as a follow-up to the computing facility. Here, the maximum transmission rate may likewise be utilized to the greatest possible extent.

In some embodiments, it is conceivable that control information for initializing the next imaging process during act S8 is already sent to the components of the rotating portion if this does not slow down, and/or could interfere with, the transmission of the second detector data. The small buffer memory may also be used for the second detector data.

In act S9, as already mentioned, the computing facility performs the preprocessing act by sorting received detector data using the selection information and converting it into a format in which subsequent reconstruction acts expect the detector data.

In act S10, these subsequent reconstruction acts use the correspondingly initialized detector data for the reconstruction of a computed tomography image dataset.

Herein, acts S9 and S10 may also at least partially already be performed during the transmission of the detector data. For example, it is conceivable that, after receipt of the first detector data, initially a provisional computed tomography image dataset is reconstructed and displayed, which is then gradually updated and improved based on the further information upon receipt of second detector data after completion of the transmission or even during transmission.

Herein, in this context, when ascertaining a computed tomography image dataset from the first detector data alone, if the maximum transmission rate is maintained therefor by omission in spatial, temporal and/or spatial frequency-related terms, interpolation may take place by linear regression, but also by more complex methods, for example, using artificial intelligence.

Figure 2:
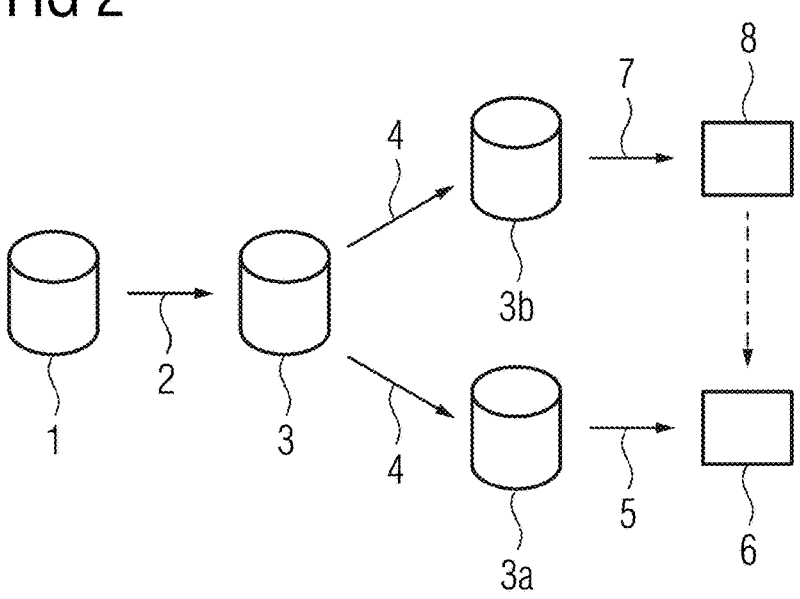
FIG. 2 depicts a sketch of the data flow according to the method in FIG. 1.

FIG. 2 illustrates the data flow according to the method shown in FIG. 1. There, initially raw data 1 is formed at the at least one detector and prepared by preparation in the preparation facility, arrow 2, to form a total set of detector data 3. In the selection unit of the preparation facility, the detector data 3 is divided into first detector data 3a of the first data stream and second detector data 3b of the second data stream according to the arrows 4. The first detector data 3a is transmitted directly to the computing facility 6 according to the arrow 5, while the second detector data 3b is forwarded as a second data stream to the temporary storage facility 8 according to the arrow 7, from where it may then likewise be transmitted to the computing facility 6 after completion of the raw data acquisition according to the dashed arrow 9.

Depending upon the specific imaging task, division into the first data stream and the second data stream (arrows 4, 5 or 4, 7) may be based on spectral sorting, temporal sorting, spatial sorting, and/or spatial frequency-based sorting. If the detector used is a counting X-ray detector that may also quantify the energy of individual X-ray quanta, the raw data measurement may take place for a plurality of energy threshold values, wherein only detector data 3 of some of the energy threshold values, in particular the at least one lowest energy threshold value, may be selected in the first data stream; the detector data 3 of other energy threshold values is sorted into the second data stream. In the case of temporal sorting, for example, only the readout result of the $n^{th}$ time step may be transmitted. With spatial sorting, a plurality of embodiments are conceivable. On the one hand, detector data 3 with lower spatial resolution may be ascertained and transmitted immediately as first detector data 3a, while higher-resolution detector data 3 may be transmitted as second detector data 3b in the follow-up. However, spatial sorting is also possible by temporarily omitting detector data 3 so that, for example, only a selection of available image rows needs to be selected in the first data stream. Herein, subgroups of an overall spatial coverage selected for the first data stream do not have to be the same for each time step, but may also, for example, alternate from time step to time step or follow a prespecified sequence of subgroups.

With regard to spatial frequencies, the preparation facility may have a transformation unit for ascertaining a spatial frequency representation of the detector data 3 so that, for example, only the detector data 3 with a spatial frequency below a spatial frequency threshold may be selected in the first data stream. It is also possible to use transmission methods such as those used in the prior art for video streaming, for example splitting according to the spatial frequencies (wavelets) that so interpolation on the receiver side produces a usable detector dataset that may be combined with the follow-up data parts, i.e., the second detector data 3b, to form a complete dataset. As already mentioned, interpolation may take place by simple linear regression, but more complex approaches are conceivable, for example using artificial intelligence. One example of this is known as "super resolution."

In a very specific example, the X-ray detector may have a detector area of 2752×288 pixels, wherein two energy thresholds are used in the counting X-ray detector. The data volume formed is clearly much too large for direct transmission. Therefore, detector data 3 with a lower spatial resolution, for example 1376×144 pixels, is ascertained for the two energy threshold values in the preparation facility. This first detector data 3a is selected in the first data stream and transmitted immediately. In addition, the spatially higher-resolution detector data is available as second detector data 3b in the temporary storage facility 8 and may be transmitted in the follow-up. Herein, it may be sufficient to transmit the detector data 3b for a single one of the energy threshold values with higher spatial resolution. Then, the detector data 3 is available on the computing facility 6 in such a way that detector data 3 of the lower energy threshold value is available once in high spatial resolution and once in low spatial resolution, but detector data of the upper energy threshold value however is only available in reduced spatial resolution.

Variations are also conceivable in which, for example, initially, only partial data of the one energy threshold value is transmitted and the like.

Figure 3:
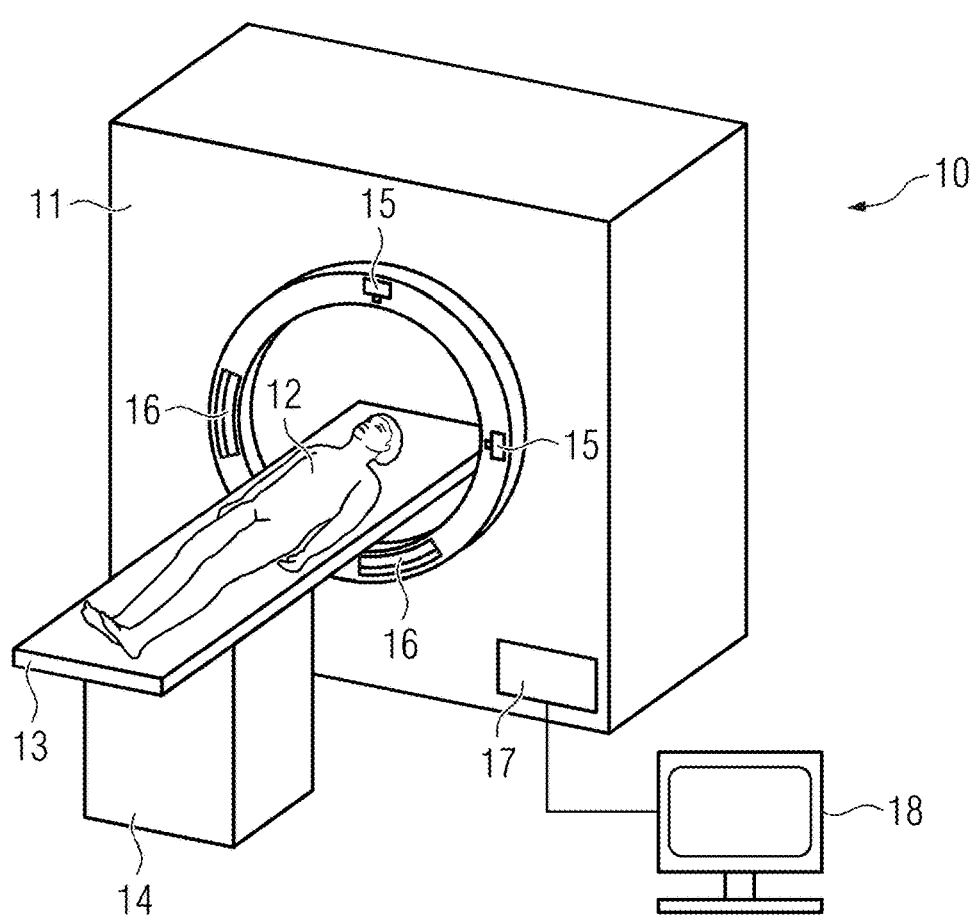
FIG. 3 depicts a schematic sketch of an example of an X-ray facility.

FIG. 3 shows a schematic sketch of a computed tomography facility 10 configured to perform the method described herein.

The computed tomography facility 10 includes a gantry 11 that has a central opening into which a patient 12 may be moved by a patient bench 13 of a patient table 14. The rotating portion includes two recording arrangements (here only indicated) with in each case an X-ray source 15 and in each case a counting X-ray detector 16. Therefore, this is a biplane computed tomography facility 10 configured for spectral imaging. The operation of the computed tomography facility 10 is controlled by a control facility 17, which may also be assigned to a display facility 18 and may include the computing facility 6.

Figure 4:
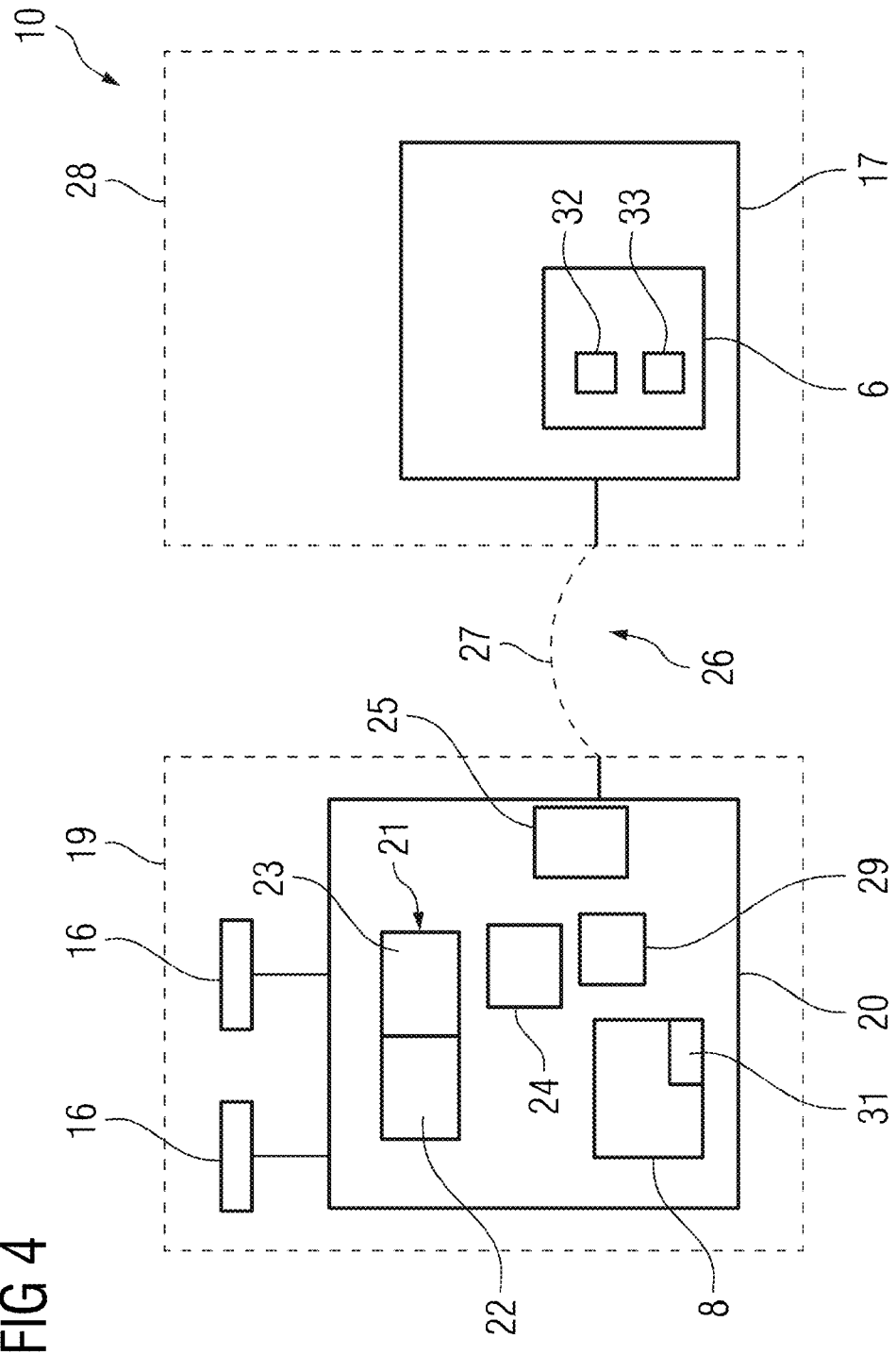
FIG. 4 depicts an example of a functional structure of a computed tomography facility and the components thereof.

In this regard, the functional structure of the computed tomography facility 10 is shown again in FIG. 4 in simplified form.

As mentioned, the computed tomography facility 10 includes a rotating portion 19 to which the two X-ray detectors 16 also belong. These supply their raw data to the preparation facility 20, which, in addition to preparation units 21—for example including the transformation unit 22 and a spatial resolution reducing unit 23—includes the selection unit 24. While, therefore, the preparation of the raw data to form the detector data 3 according to act S3 takes place by the preparation units 21, the selection and division of the detector 3 into the data streams according to act S4 takes place in the selection unit 24. The first data stream is forwarded to a transmission unit 25 that transmits the first detector data 3a directly via the communication path 26 with the wireless communication link 27 to the control facility 17 in the fixed portion 28, and hence also to the computing facility 6 that forms part of the control facility 17. In other words, the transmission unit 25 executes act S5.

The second data stream is forwarded to a temporary storage unit 29 that temporarily stores the second detector data 3b in the temporary storage facility 8 of the preparation facility 20 according to act S6. Herein, part of the temporary storage facility 8 may also be reserved as a buffer memory 31 for resending data packets for the transmission unit 25.

On completion of the raw data acquisition and the transmission of the first data stream to the computing facility 6, the transmission unit 25 may also transmit the second detector data 3b via the communication path 26 to the computing facility 6 (act S8).

The computing facility 6 may have an initialization unit 32 for performing the initialization act S9 and a reconstruction unit 33 for performing act S10, i.e., the reconstruction of a computed tomography image dataset.

Although the disclosure has been illustrated and described in greater detail by the embodiments, the disclosure is not restricted by the disclosed examples and other variations may be derived herefrom by the person skilled in the art without departing from the scope of protection of the disclosure.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a computed tomography facility having a rotatable portion with at least one X-ray detector and a portion fixed relative to the rotatable portion with a computing facility configured to process detector data recorded with the at least one X-ray detector, wherein the at least one X-ray detector is assigned a preparation facility for ascertaining detector data to be transmitted to the computing facility via a communication path from raw data of the at least one X-ray detector and the communication path has a wireless communication link with a maximum transmission rate, and wherein, during an imaging process, the method comprises:

dividing, by a selection unit of the preparation facility, the detector data into: (1) a first data stream with first detector data for reconstruction of an evaluable computed tomography image dataset after completion of raw data acquisition with the at least one X-ray detector with a data transmission rate corresponding at most to the maximum transmission rate; and (2) a second data stream comprising remaining detector data as second detector data;

transferring the first data stream as a real-time transmission directly to the computing facility via the communication path;

storing the second detector data temporarily in a temporary storage facility; and transmitting the second detector data to the computing facility via the communication path after completion of the raw data acquisition with the at least one X-ray detector and the transferring of the first data stream, wherein, for transmissions via the communication path, a buffer memory is used that allows a data packet to be resent in an event of a faulty transmission, and wherein the buffer memory is implemented as part of the temporary storage facility reserved for this purpose.

2. The method of claim 1, wherein the first data stream comprises the first detector data that is at least partially reduced in spatial resolution and/or spatial coverage compared to all of the detector data.

3. The method of claim 2, wherein a prespecified overall spatial coverage of the detector data is split into at least two subgroups, and wherein the raw data acquisition takes place in time steps and in each case only detector data of one subgroup of the at least two subgroups is selected into the first data stream in successive time steps according to a prespecified sequence of the at least two subgroups.

4. The method of claim 1, wherein the preparation facility comprises a transformation unit configured to ascertain a spatial frequency representation of the detector data, and wherein only detector data with spatial frequencies that is below a spatial frequency threshold is sorted into the first data stream.

5. The method of claim 1, wherein, when detector data is omitted spatially, temporally, frequency-based, or a combination thereof for the first data stream, on the reconstruction of a computed tomography image dataset from the detector data of the first data stream alone, at least a part of the omitted detector data is reconstructed by interpolation and/ or extrapolation.

6. The method of claim 1, wherein the computed tomography facility is configured for spectral imaging, wherein the detector data comprises partial data assigned to a plurality of energy threshold values as energy parameter values, and wherein the first data stream only contains partial data for some energy threshold values less than all of the plurality of energy threshold values.

7. The method of claim 1, wherein the division is carried out in order to make a greatest possible use of the maximum transmission rate.

8. The method of claim 1, wherein the selection unit carries out the division according to at least one selection parameter prespecified by a control facility of the computed tomography facility.

9. The method of claim 8, wherein the at least one selection parameter is assigned to each selectable recording protocol specifying acquisition parameters for the raw data acquisition and/or preparation parameters for the preparation and transferred to the preparation facility and set at the preparation facility before a start of the raw data acquisition.

10. The method of claim 8, wherein the at least one selection parameter and/or selection information describing the division into the data streams is also transferred to the computing facility when, in an initialization act, the received detector data of the first data stream and the second data stream is combined to form a detector dataset suitable as input data for subsequent data processing operations of the computing facility.

11. The method of claim 1, wherein, during the transmission of the second detector data, initialization information for the next imaging process is already transferred to the rotating portion.

12. The method of claim 1, wherein, in an event of only partial transmission of the second detector data, which comprises additional information compared to the first detector data, due to an error, the computing facility is configured to add the additional information in the computed tomography image dataset at least with respect to a transmitted part.

13. The method of claim 12, wherein the error is a system failure.

14. A method for operating a computed tomography facility having a rotatable portion with at least one X-ray detector and a portion fixed relative to the rotatable portion with a computing facility configured to process detector data recorded with the at least one X-ray detector, wherein the at least one X-ray detector is assigned a preparation facility for ascertaining detector data to be transmitted to the computing facility via a communication path from raw data of the at least one X-ray detector and the communication path has a wireless communication link with a maximum transmission rate, and wherein, during an imaging process, the method comprises:

dividing, by a selection unit of the preparation facility, the detector data into: (1) a first data stream with first detector data for reconstruction of an evaluable computed tomography image dataset after completion of raw data acquisition with the at least one X-ray detector with a data transmission rate corresponding at most to the maximum transmission rate; and (2) a second data stream comprising remaining detector data as second detector data;

transferring the first data stream as a real-time transmission directly to the computing facility via the communication path;

storing the second detector data temporarily in a temporary storage facility; and transmitting the second detector data to the computing facility via the communication path after completion of the raw data acquisition with the at least one X-ray detector and the transferring of the first data stream, wherein a temporal resolution of the first detector data is lower than a temporal resolution of all of the detector data.

15. A computed tomography facility comprising:

a computing facility;

at least one X-ray detector;

a communication path having a wireless communication link with a maximum transmission rate;

a preparation facility configured to ascertain detector data to be transmitted to the computing facility via the communication path from raw data of the at least one X-ray detector; and a rotatable portion with the at least one X-ray detector and a portion that is fixed relative to the rotatable portion with the computing facility configured to process detector data recorded with the at least one X-ray detector, wherein the at least one X-ray detector is assigned the preparation facility, wherein the preparation facility comprises:

a selection unit configured to divide the detector data of an imaging process into: (1) a first data stream with first detector data for reconstruction of an evaluable computed tomography image dataset after completion of a raw data acquisition with the at least one X-ray detector with a data transmission rate corresponding at most to the maximum transmission rate; and (2) a second data stream comprising remaining detector data as second detector data;

a temporary storage unit configured to temporarily store the second detector data of the second data stream in a temporary storage facility; and a transmission unit for direct real-time transmission of the first data stream via the communication path to the computing facility and, after completion of the raw data acquisition of the imaging process, for transmission of the second detector data via the communication path to the computing facility, wherein, for transmissions via the communication path, a buffer memory is configured to be used that allows a data packet to be resent in an event of a faulty transmission, and wherein the buffer memory is implemented as part of the temporary storage facility reserved for this purpose.

\* \* \* \* \*